(12) United States Patent
Bonnet et al.

(10) Patent No.: US 6,246,910 B1
(45) Date of Patent: Jun. 12, 2001

(54) RATE RESPONSIVE ACTIVE IMPLANTABLE MEDICAL DEVICE SUCH AS A PACEMAKER, DEFIBRILLATOR AND/OR CARDIOVERTOR, INCLUDING THE MULTISITE TYPE

(75) Inventors: Jean-Luc Bonnet, Montrouge; Marcel Limousin, Paris, both of (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/339,359

(22) Filed: Jun. 23, 1999

(30) Foreign Application Priority Data

Jun. 26, 1998 (FR) .................................................. 98 08118

(51) Int. Cl.$^7$ .................................................. A61N 1/365
(52) U.S. Cl. .................................................. 607/18
(58) Field of Search .................................. 607/18, 17, 19, 607/20, 21, 22, 23

(56) References Cited

U.S. PATENT DOCUMENTS

| | | | |
|---|---|---|---|
| 5,003,975 | 4/1991 | Hafelfinger et al. | 128/419 |
| 5,154,170 | 10/1992 | Bennett et al. | 128/419 |
| 5,330,505 | 7/1994 | Cohen | 607/6 |
| 5,423,869 | 6/1995 | Poore et al. | 607/18 |
| 5,476,485 | 12/1995 | Weinberg et al. | 607/28 |
| 5,562,711 | 10/1996 | Yerich et al. | 607/17 |

FOREIGN PATENT DOCUMENTS

| | | | |
|---|---|---|---|
| 0 654 285 | 5/1985 | (EP) | A61N/1/365 |
| 0 804 939 | 11/1997 | (EP) | A61N/1/365 |

*Primary Examiner*—Scott M. Getzow
(74) *Attorney, Agent, or Firm*—Orrick, Herrington & Sutcliffe LLP

(57) ABSTRACT

A rate responsive active implantable medical device having at least one effort sensor, measuring a parameter which is predominantly physiological (VE) and delivering an output signal which is a function of the effort developed by a patient carrying the device, and at least one activity sensor, measuring a parameter which predominantly physical. The devices operates to (a) measure periodically at the two sensors "couples of values" (12, 14, 16; 22, 24, 26) corresponding to a given level of effort developed by the patient; (b) establish a characteristic function of the measured couples of values (10, 20), and (c) evaluate over the course of time this established characteristic, by seeking a possible increase in the signals delivered by the effort sensor as compared to the signals delivered by the activity sensor, indicative of the patient's metabolic demand (cardiac output requirements). The device preferably is implemented in a multisite type pacemaker in which the control of stimulation and/or the configuration of the stimulation sites is modified in the even of an excessive increase in the metabolic demand of the patient.

10 Claims, 1 Drawing Sheet

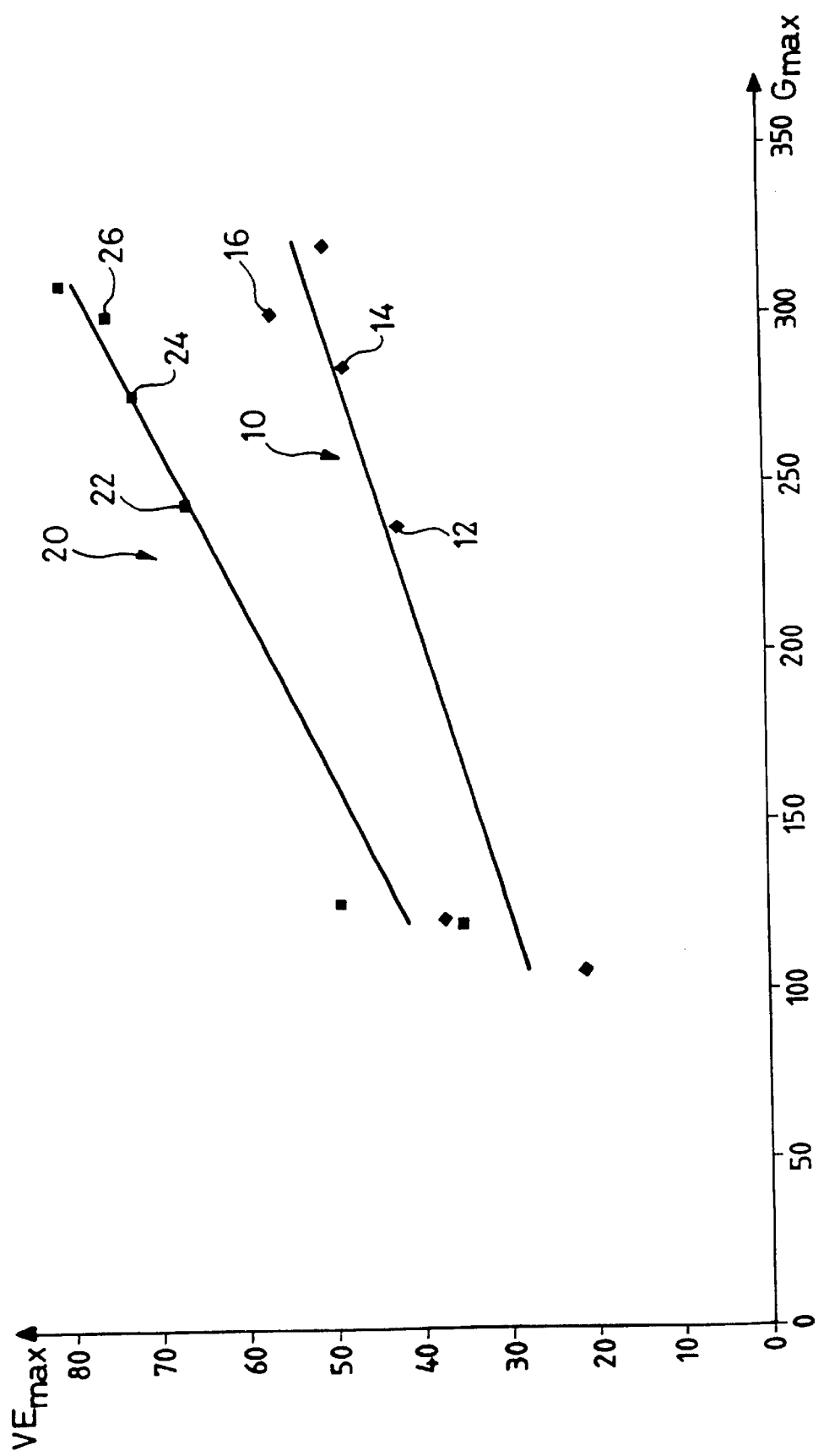

RATE RESPONSIVE ACTIVE IMPLANTABLE MEDICAL DEVICE SUCH AS A PACEMAKER, DEFIBRILLATOR AND/OR CARDIOVERTOR, INCLUDING THE MULTISITE TYPE

FIELD OF THE INVENTION

The present invention relates to "active implantable medical devices" as defined, for example, by the Jun. 20, 1990 Directive 90/385/CEE of the Council of the European Communities, including but not limited to pacemaker devices, defibrillators and/or cardiovertors which are able to deliver to the heart electric pulses of low energy for the treatment of heart rate disorders. It more particularly relates to devices having an operation controlled by a sensed parameter using an appropriate sensor, such as rate responsive devices.

BACKGROUND OF THE INVENTION

There are active implantable medical devices which are known to adapt their actions, for example, the stimulation frequency, to a measured or calculated value of a parameter that is representative of the metabolic needs of the person in which the device is implanted. One sensor which is generally used to measure such a parameter is the so-called minute volume or minute ventilation sensor (often called "sensor MV" or "sensor VE").

EP-A-0 804 939 describes a pacemaker in which the signals delivered by a minute ventilation sensor are used in addition to a control function, to diagnose the decompensation (i.e., the deterioration or worsening) of the cardiac insufficiency and to cause a modification of the programming of the pacemaker.

One problem with this device is that it presents the disadvantage of not taking into account the real level of activity of the patient. Indeed, it is known that persons with cardiac insufficiency have a deteriorated ventilatory function because of their pathology. As a result, these patients will present, during an effort level of activity (i.e., a level of activity above rest), an oxygen consumption ($VO_2$) which is lower than that of healthy patients; on the other hand, the heart rate and minute ventilation of these patients will increase significantly more than is the case for healthy patients, for the same level of activity.

Thus, a relative or absolute variation in time of the signals detected by the minute ventilation sensor, or in a more general way, by a different physiological sensor which is provided to give an adequate representation of the metabolic needs of the patient, can be due to cardiac insufficiency or to a simple change of the activity level of the patient.

It also has been proposed, for example, in EP-A-0 750 920 and its corresponding U.S. Pat. No. 5,722,996 (commonly assigned to the assignee of this application, ELA Méedical, Montrouge, France) to combine the information delivered by two sensors, one physiological (typically a minute ventilation sensor), the other of physical activity (typically an accelerometer, often called "sensor G"). The two sensors operate a so-called "cross monitoring" of their respective indications, and the pacemaker combines the information from the two sensors as described therein to control the heart rate. However, this device also does not take into account the evolution over the long term of the pathology of the patient, who can present greater or lesser cardiac decompensation over time.

This pathology can indeed evolve according to various factors such as the effectiveness of cardiac stimulation, the effectiveness of the drugs delivered, or the food, or the presence of atrial and/or ventricular arrhythmias.

OBJECTS AND SUMMARY OF THE INVENTION

It is, therefore, an object of this invention to propose a pacemaker which is able to follow the evolution of the patient over the course of time so as to give an adequate representation of the patient's real metabolic needs. In the event of an aggravation of or an improvement in the patient's condition, the pacemaker will then be able advantageously to modify its operation, for example, by reprogramming one or more of its functions. This reprogramming can be automatic or physician initiated.

One aspect of the invention is directed to a device of the type with two parameter sensors, e.g., comprising at least one sensor of effort, measuring a parameter which is predominantly physiological and delivering an output signal which is a function of the effort developed by a patient wearing the device, and at least one sensor of activity, measuring a parameter which is predominantly physical, and having an output signal which is a function of the patient's activity level. Such a device is described in the aforementioned EP-A-0 750 920 (U.S. Pat. No. 5,722,996), the disclosure of which is hereby incorporated hereinby by reference in its entirety.

In accordance with this aspect of the invention, this device also includes a processing means for analyzing the acquired effort and activity related data to evaluate the evolution over time of the patient's effort and activity levels. In one embodiment, the analysis means operates: (a) to measure periodically using the two sensors "couples of values" corresponding to a level of effort/activity developed by the patient, (b) to establish a characteristic function of the couples of values thus measured, and (c) to evaluate the evolution over the course of time of this established characteristic. Preferably, the evolution is evaluated by seeking a possible increase in the signals delivered by the effort sensor as compared to the signals delivered by the activity sensor.

Very advantageously, the analysis means also operates: (d) to modify the programming of the device when the results of the subpart (c) evaluation indicate an increase in the signals delivered by the effort sensor beyond a given threshold compared to the signals delivered by the activity sensor.

The present invention is particularly applicable to a device including the functionality of a pacemaker of the "multisite" type, i.e., in which electrodes are placed in a plurality of distinct myocardial stimulation sites, and the control of the stimulation and/or the configuration of the stimulation sites are modified when the results of the evaluation indicate an increase beyond a given threshold in the output signals delivered by the effort sensor as compared to the output signals of the activity sensor.

In one embodiment, the analysis means can evaluate the shift of the established characteristic in the direction of increasing effort, or evaluate the increase in an effort/activity slope of the established characteristic. Optionally, this evaluation can be operated regularly, i.e., at periodic intervals (typically, daily or every selected number of cardiac cycles).

BRIEF DESCRIPTION OF THE DRAWINGS

Other features, characteristics and advantages of the present invention will appear to a person of ordinary skill in the art in view of the following detailed description, made with reference to the annexed drawing, which illustrates the minute ventilation and established activity characteristic, determined for two different consecutive periods.

DETAILED DESCRIPTION OF THE DRAWINGS

For illustrative purposes, the present invention will be described within the framework of a configurable multisite type pacemaker, for example, the one described in French Patent Application No. 97-16378 of Dec. 23, 1997, published Jun. 25, 1999 under number FR 2772622 and its corresponding U.S. patent application No. 09/218,678, which is copending and commonly assigned and incorporated in its entirety herein by reference, entitled "active implantable medical device, in particular pacemaker, defibrillator and/or cardiovertor, of multisite type configurable" in the name of ELA Médical. A teaching of this application is commercially implemented in the device known as the model Chorum 7336 pacemaker marketed by ELA Médical.

Typically, in such multisite devices, an endocardial probe (also called a "lead" or "catheter") is placed in the right ventricle, as in the traditional technique for cardiac stimulation, and a second probe is placed at the level of the left ventricle (for example, by insertion through the coronary sinus and the coronary venous network). Additional probes also can be installed to allow for atrial (single or double) stimulation, to supplement the double ventricular stimulation. The invention thus evaluates at periodic intervals the degree of decompensation of the patient on the basis of deterioration or improvement of the ventilatory function associated with cardiac pathology, compared to the signals delivered by the activity sensor.

The invention primarily proposes to combine the information from two sensors, one physiological and the other physical, to determine if an amplitude variation of the physiological sensor over the course of time results from a simple change of the activity level of the patient or, on the contrary, of an aggravation of the cardiac insufficiency.

It should be understood by a person skilled in the art that the term "physiological sensor" refers to a sensor designed (or employed) to give an adequate representation of the metabolic needs of the patient at a given moment, typically a minute ventilation sensor (MV) according to a well-known, traditional technique, for example, as described in EP-A-0 151 689 and its counterpart U.S. Pat. No. 4,596,251.

It also should be understood by a person skilled in the art that the term "activity sensor" refers to a sensor allowing one to detect quickly a change of the activity of the wearer of the apparatus, typically an accelerometer (sensor G), as taught, for example, in EP-A-0 550 293 and its counterpart U.S. Pat. No. 5,330,510 (ELA Médical) or EP-A-0 750 920 and its counterpart U.S. Pat. No. 5,722,996 (ELA Médical), the latter describing a pacemaker with dual sensors, one physiological (sensor MV) and the other physical (activity sensor G).

From a physiological point of view, one starts from the principle that for a patient undergoing exercise, there is a proportionality between the level of activity, measured with the sensor G, and the physiological level, measured with sensor MV. For each effort, one retains only the relation between the maximum level of acceleration G realized (Gmax) and the maximum level of minute ventilation VE realized (VEmax). One thus obtains for each measured or determined effort a "couple of values", namely (Gmax, VEmax).

If one represents, as is the case, on the drawing, by points 12, 14, 16 . . . (only 3 datapoints shown) these various couples being measured during the course of one day, one obtains because of the proportionality a curve which can be modeled by a line 10. If this relation is not linear, the line will not be optimal, but the tendency will be respected (the line can, for example, be determined by a linear regression calculation). However, it is know that, for the same level of effort (identical activity G), a patient having a cardiac insufficiency patient will over-ventilate compared to a healthy patient.

Thus, given two comparable patients, one healthy and the other one having a cardiac insufficiency, who reach during an effort the same level of activity (identical Gmax), the VEmax value of the first will be lower than VEmax of the second (this assertion being of course true only in a statistical respect, for a population).

Now, if one considers the same patient followed over time, this patient is treated by a cardiac pacemaker which compensates partly for the patient's pathology. The patient can present over the course of time more or less cardiac decompensation, evolving according to various factors such as the effectiveness of cardiac stimulation, the effectiveness of any drugs delivered, food or the presence of atrial and/or ventricular arrhythmias. In this case, from one day to another, the patient could be compared with himself or with herself, and a trend (long term and/or short term) can be identified.

Thus, for phases of increasing cardiac decompensation, one will observe an increase in VEmax for same levels of effort Gmax. In other words, the patient will have produced a greater ventilation for the same effort, which means that patient's pathological state has worsened.

If one traces the characteristics corresponding from one day to the next on the diagram of the drawing, one obtains, for example, an established characteristic 10 one day when the cardiac insufficiency is moderate, and an established characteristic in the form of a curve 20 (determined from points 22, 24, 26 . . . in the same manner as curve 10 starting from the given points 12, 14, 16 . . . ) on a different day when the patient's cardiac insufficiency is worse. One notes that the curve 20 is moved upwards relative to curve 10, i.e., it has the larger values of VE for the same levels of G.

The pacemaker can thus determine each day a curve, such as curves 10 or 20, and possibly deduce from this curve an established characteristic index, such as the shift of the characteristic upwardly (in the direction of increasing VEmax) or, as appropriate in the given circumstances, a variation of the slope of the established characteristic.

After a few days of stable patient behavior (i.e., when the successively determined lines 10 and 20 are essentially unchanged), the processor is able to determine a standard of reference index of the patient (e.g., an average), in relation to which a distinguishable variation of this index will be a sign of a cardiac decompensation. This information can be stored in memory in the pacemaker, and transmitted to the physician by telemetry during a clinical examination of the patient, in order to carry out a possible reprogramming of the pacemaker.

One can, in addition, provide advantageously that the pacemaker adapts its operation to the variation of the level of decompensation. In the case of a multisite pacemaker, the pacemaker can optionally and advantageously modify the configuration of the stimulation sites, as is proposed, for example, in French Application 97 16378 and U.S. application Ser. No. 09/218,678, mentioned above.

One skilled in the art will appreciate that the present invention can be practiced by other than the described embodiment, which is presented for the purposes of illustration and not of limitation.

We claim:

1. A rate responsive active implantable medical device for use in a patient, comprising:

at least one effort sensor operable to measure a predominantly physiological parameter of a patient and having an output signal corresponding to an effort level of the patient;

at least one activity sensor operable to measure a predominantly physical parameter of patient and having an output signal corresponding to an activity level of the patient;

means for analyzing the at least one effort sensor output signal and the at least one activity sensor output signal, said means comprising:

means for periodically measuring said at least one effort sensor output signal and at least one activity sensor output signal and determining therefrom couples of values, each said couple of value corresponding to a given level of effort and activity developed by the patient at said measurement;

means for establishing a characteristic function of said determined couples of value for a first time period;

means for comparing an established characteristic function corresponding to a time period to a subsequent established characteristic function corresponding to a subsequent time period;

means for determining whether there is an evolution of said established characteristic function in response to at least one of said comparisons of an established characteristic function to a subsequent established characteristic function; and means for determining a degree of deterioration of the patient in response to said evolution of said established characteristic function.

2. The device of claim 1 wherein the means for determining whether there is an evolution further comprises means for determining an increase in the effort sensor output signals relative to the corresponding activity sensor output signals of said couples of values.

3. The device of claim 2 wherein the means for determining whether there is an evolution further comprises means for determining an increase in the effort sensor output signals relative to the corresponding activity sensor output signals of said couples of values, wherein said activity sensor output signals correspond to the same patient activity level.

4. The device of claim 2, wherein the rate responsive device has a programmable function, and wherein the analyzing means further comprises:

means for comparing the increase in the effort sensor output signals relative to the activity sensor output signals to a predetermined threshold;

means for indicating the programmable function should be modified in response to said increase exceeding said predetermined threshold.

5. The device of claim 4 wherein the analyzing means further comprises means for modifying the programmable function in response to said indicating means.

6. The device of claim 5, further comprising:

at least a first electrode and a second electrode to be placed in corresponding distinct myocardial stimulation sites;

first means for controlling the stimulation of the distinct myocardial sites;

second means for controlling the configuration of the electrodes for stimulating the distinct myocardial sites;

wherein the modifying means further comprises means for modifying one of the first controlling means and second controlling means to modify one of the stimulation of and the configuration of the distinct myocardial sites to be stimulated in response to said increase exceeding said predetermined threshold.

7. The device of claim 1, wherein the means for determining whether there is an evolution further comprises means for detecting a shift in the established characteristic function in a direction of increasing patient effort.

8. The device of claim 1 wherein the means for establishing a characteristic function further comprises means for determining a slope of the activity sensor output signal relative to the effort sensor output signal, and wherein the means for determining whether there is an evolution further comprises means for determining an increase in the determined slope.

9. The device of claim 1 further comprising means for regularly periodically causing the means for determining whether there is an evolution to determine whether there is an evolution.

10. The device of claim 9 wherein the means for regularly periodically causing causes the means for determining whether there is an evolution to determine whether there is an evolution daily.

* * * * *

UNITED STATES PATENT AND TRADEMARK OFFICE
CERTIFICATE OF CORRECTION

PATENT NO. : 6,246,910 B1
DATED : June 12, 2001
INVENTOR(S) : Jean-Luc Bonnet and Marcel Limousin It is certified that error appears in the above-identified patent and that said Letters Patent is hereby corrected as shown below:

Column 1,
Line 54, delete "Méedical" and insert -- Médical -- therefor;

Column 2,
Line 26, delete "hereinby" and insert -- herein -- therefor;

Column 4,
Line 8, delete "know that" and insert -- known that -- therefor;
Line 10, delete "insufficiency patient" and insert -- insufficiency -- therefor; and Column 5,
Line 25, delete "of value" and insert -- of values -- therefor.

Signed and Sealed this

Twenty-sixth Day of July, 2005

JON W. DUDAS
*Director of the United States Patent and Trademark Office*